BICOLORED HYBRID TEA ROSE

Filed Oct. 21, 1965 2 Sheets-Sheet 1

HARRY E. PALMER
INVENTOR
BY
BUCKHORN, BLORE, KLARQUIST & SPARKMAN
ATTORNEYS

BICOLORED HYBRID TEA ROSE

Filed Oct. 21, 1965 2 Sheets-Sheet 2

HARRY E. PALMER
INVENTOR

BUCKHORN, BLORE, KLARQUIST & SPARKMAN
ATTORNEYS

United States Patent Office

Plant Pat. 2,706
Patented Jan. 31, 1967

2,706
BICOLORED HYBRID TEA ROSE
Harry E. Palmer, 4841 NE. 39th Ave.,
Portland, Oreg. 97211
Filed Oct. 21, 1965, Ser. No. 500,458
1 Claim. (Cl. Plt.—11)

The present invention relates to a new and distinct variety of rose plant of the hybrid tea class, and more specifically to a sport of Rose Gaujard. (Plant Patent 1,829.)

Some of the primary distinguishing characteristics of my rose plant are (1) the distinct delicate pink and white-cream bicoloration of the flowers, (2) the abundance of such flowers and the large number of petals on a flower and the superior form, structure and disposition thereof, (3) the free and basically unretracted wavy form of the free margins of the petals, (4) the changes in petal coloration that occur as the flowers progressively open and age, and thus (5) the simultaneous presence on the bush of an abundance of flowers in different stages and extent of coloration; such petals, except for the outermost false petals of the bud, being initially entirely cream-white, but becoming tinged delicately with pink at the free wavy edges thereof as the petals are exposed, and wherein the coloration deepens as the petals age and wherein the coloration suffuses toward but terminates distinctly short of the bases of the petals during aging of the petals, so that the extent of suffusion and depth of degree of coloration are roughly proportional to the times of exposure of the various petals.

My rose plant is also distinguished by the large number of canes produced (up to 10 or 12 canes), by its strong and vigorous growing habits, by its resistance to disease and climatic changes, by the absence of a split center, which fault is not infrequently found in Rose Gaujard, and by the production of at least some flowers on practically every bush which are of such outstanding form and symmetry and have such high centers that they may be used for show or exhibition purposes.

Figure 1:
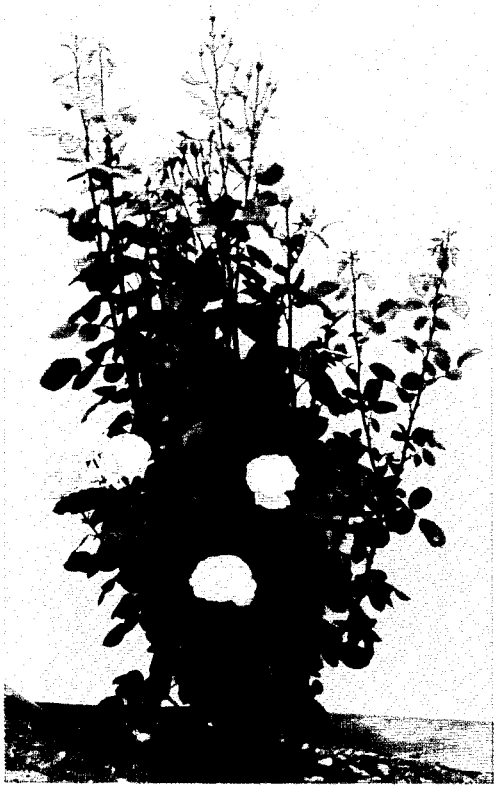
FIG. 1 is a reproduction of a colored photograph of a bush of my invention, the bush being about five feet tall and about one and three-quarters years old from budding (onto one year old understock)
Figure 5:
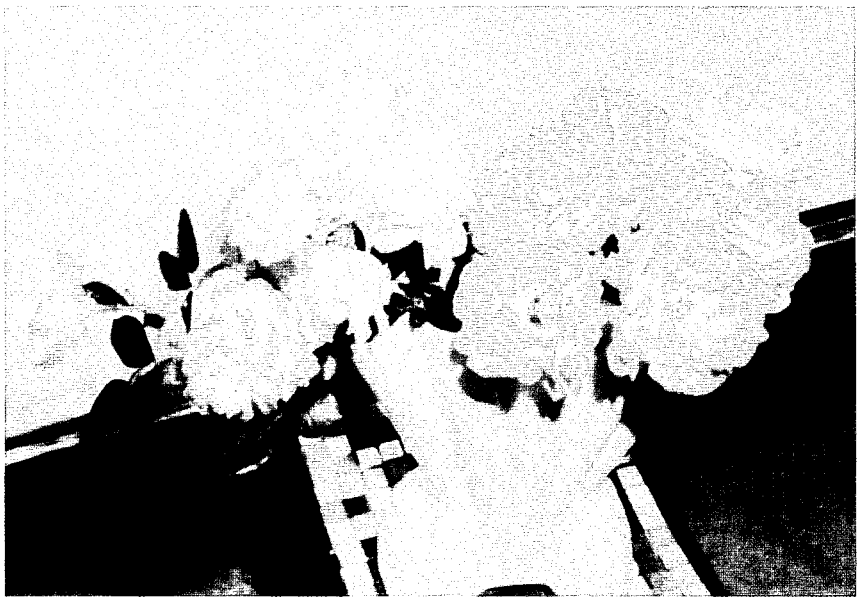
FIG. 5 is a colored photograph of rose flowers of my invention.

The colored photographs referred to above (except for FIG. 5) were taken by a commercial photographer around 5:00–6:00 p.m. in June 1965. Such colored photographs and the resulting colored reproductions (which are part of this application) are the best efforts of such commercial photographer to show the true color of my bush and its rose flowers, but the delicate pink shade of my flower evidently could not be accurately reproduced, because the pink-red color shown, particularly in FIG. 3, is too hard, while the pink and pink-red colors in FIG. 1 are less hard and more closely approach, but fall short of the true delicate pink or pink-red color of the rose flower of my plant. FIG. 5 is a colored photograph I took myself and I believe the colors shown more closely approximate the true colors of my rose than FIGS. 1–3.

As the pinkish color emerges on the free edges or margins of a petal of my rose, it is soon near that of block I–3 (and adjacent blocks) of plate 49 of Maerz and Paul Dictionary of Color, second edition, 1950. As the petal ages, the pink color darkens (and suffuses) and is near that of block J–8 (and/or adjacent blocks) of plate 52 of said dictionary.

The strong growing habits of my plant are evident from FIG. 1, wherein the plant shown is about five feet tall. It was budded in about September 1963, pruned and transplanted in November 1964 to its present position. Since the photograph was taken in June 1965, it is evident that my bush grew from bud to a height of five feet in about a year and three-quarters. The understock was about a year old, and so the overall age of the budded plant (including the age of the understock) would be about two and three-quarters years.

FIG. 1 also shows the production of flowers directly on long single stems (the lower four or five flowers in FIG. 1) and shows at the upper portion of the bush the production of candelabra stem groups which are carrying buds.

Figure 2:
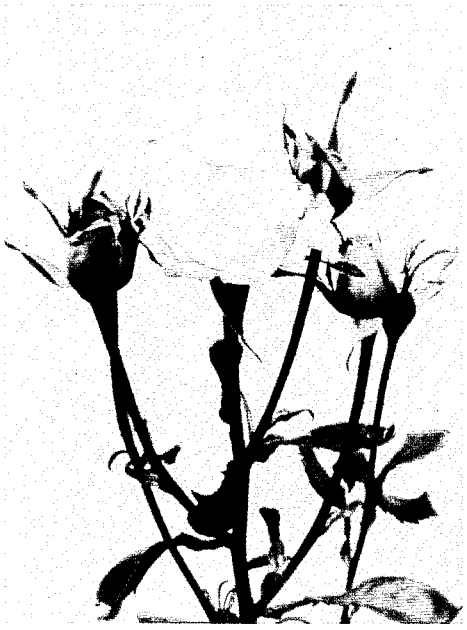
FIG. 2 is a reproduction of a colored photograph on an enlarged scale showing a candelabra stem group including a one-third open bud and a number of closed buds.
Figure 3:
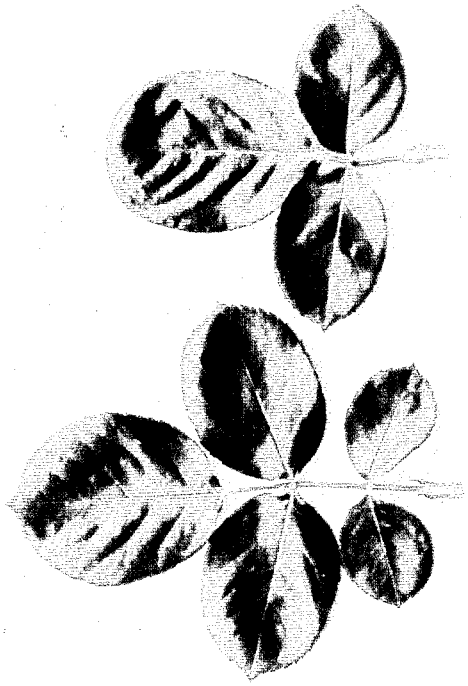
FIG. 3 is a reproduction of a colored photograph of a full blown rose flower of my invention.

FIG. 2 shows a candelabra stem group with one bud one-third open and the remaining buds closed. The outer red to pink-red false petals of the closed buds enclose the cream-white true petals, the color of the latter being fairly well shown in FIG. 2 but perhaps a shade too much toward the cream color. This figure also shows that shortly after exposure, the petals assume a delicate pink color on the free (outer or upper) edges thereof, the coloring in FIG. 2 being a somewhat harder red cast than is actually the case.

The cream-white color of the major portions of my petals are near that of block C–2 (and/or adjacent blocks) of plate 9 of said color dictionary. The base portions of the petal assume a yellower cast, being near to that of block H–2 (and/or adjacent blocks) of plate 41 of said dictionary, the base color suffusing with the cream-white of the remainder of the petal.

FIG. 3 shows the generally unretracted nature of the free margins of the petals and also shows the wavy nature of such free margins.

Figure 4:
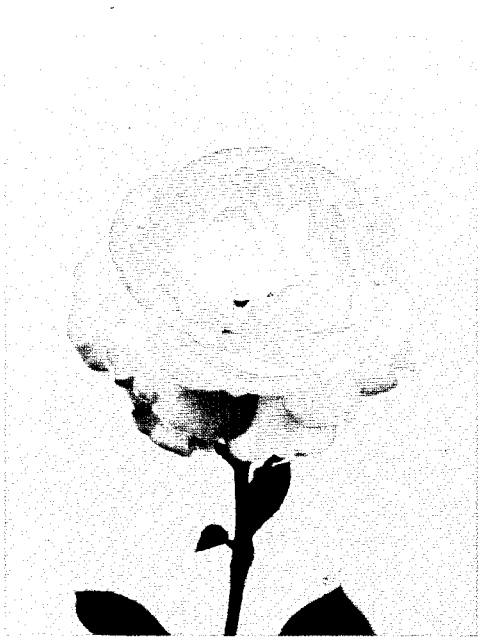
FIG. 4 is a view of some leaves of a bush of my invention.

FIG. 4 accurately portrays the typical shape of the leaves of my bush, but the color of the leaves shown is deeper than is actually the case, the leaves of my bush being about the same shade of green as that of the leaves of Rose Gaujard, but usually slightly lighter. It is evident from FIG. 4 that the leaves of my bush are of generally rounded form and terminate in rounded fashion with only a short tip produced.

I discovered my plant in my own garden in Portland, Oregon. The plant itself was purchased by me from a nursery in Portland, Oregon in potted condition. The plant at the time of purchase had three canes, one of which bore a rose flower which was unmistakably a Rose Gaujard flower, and the plant was sold as a Rose Gaujard. After purchase, I removed it from its pot and planted it in my garden. Subsequently one of the canes produced the flower of my new variety which was obviously a superior flower and a superior cane. I subsequently cut off the other two canes and still have this plant in my garden.

I next removed a cutting from the sport cane (the original cane having now produced a number of canes of its own) and rooted the cutting in my garden and found that it rooted easily and produced an excellent plant. Then I budded my variety on some standard understock (it may have been multiflora) and the budding was successful. Subsequently further budding was done for me by a nursery in Portland, Oregon from buds removed by me and supplied to the nursery for such purposes. Such budding has proved successful using one year old multiflora japonica root or understock.

I soon found out that the growing characteristics of my plant were definitely superior to those of Rose Gaujard in that (1) my plant is a stronger and more vigorous grower; (2) my plant produces many more canes; (3) the canes of my plant are upright and generally together while those of Rose Gaujard tend to spread out; (4) some of the canes of my bush have single stems bearing flowers, while other canes on the same bush produce candelabra stems bearing flowers, while Rose Gaujard does not produce candelabra stems, at least to any appreciable extent; (5) the leaves of my bush are more rounded at the free ends than those of Rose Gaujard; (6) my bush is almost a constant producer of many flowers, and not infrequently my bush will carry at one time as many as two dozen blooms and buds.

The following is a detailed description of my new variety, with color terminology being of ordinary dictionary significance except as heretofore specifically set forth.

Type: Hardy; bush; outdoor; for cut flowers and garden decoration and the not infrequent production of flowers suitable for show and exhibition purposes.

Class: Hybrid tea.

Breeding: Sport of Rose Gaujard.

Propagation: Holds its distingushing characteristics through succeeding propagations by budding (the characteristics of my bush have proved fixed).

*Flower*

Locality where grown and observed: Portland, Oregon, U.S.A.

Bud:

*Size.*—Medium.

*Form.*—Pointed.

*Color.*—White with bright pink or light red edging (as specifically heretofore described), with the outer petals slowly showing more pink as the petals start to roll back or unfurl; inside of petals light pink to light red with outside of petals white, some slight variations of degree of color.

*Sepals.*—Smooth edge except for side hairlike projection from side of each sepal as they open; hoodlike extension of sepals above bud; curl back soon after bud begins to show color.

*Calyx.*—Pear shaped, slender, smooth, some mild odor.

*Peduncle.*—Very long, stiff, smooth to mildly rough, color is bronzy.

*Opening.*—Bud opens well but slowly and color intensifies with growth; is not affected by adverse weather conditions.

Bloom:

*Size.*—Large, 5 to 5½ inches when fully expanded.

*Borne.*—Several together in clusters and singly on long stems; clusters are pyramidal, noticeably symmetrical with some of the side buds being borne on stems up to 9 or 10 inches.

*Stems.*—Long and strong.

*Form.*—When first open, medium high center; permanent; opens with petals curling and waving partially back and then retains this open, curling form for days on the bush.

*Petalage.*—Double, up to 50 or more petals, inside petals smaller.

*Color.*—White, bordered and suffused with bright pink-red (as specifically previously described) with upper half of petals changing to pink-red over white; red shaded to pink.

*Variegations.*—Identified above.

*Discoloration.*—No real discoloration until petals drop cleanly. Actually, the color becomes intensified pink-red over white.

Petals:

*Texture.*—Medium thick, firm yet soft. Not affected by wet weather. Average amount of wilting in hot weather approaching the 90's in the clusters, but those on single stems hold up better. No rain spotting or sunburn noted.

*Appearance.*—Inside is velvety, outside is velvety.

*Form.*—Oval and occasionally scalloped.

*Arrangement.*—Informal with rags in the center. Few petaloids in the center.

*Persistence.*—Drop off cleanly.

*Fragrance.*—Slight, old rose fragrance.

*Lastingness.*—On the plant — very long; as cut flowers—very long.

Sexual organs:

*Stamens, anthers.* — Small, many, Color — light brown. Arrangement—regular around styles.

*Stamens, filaments.*—Short, yellow.

*Pollen.*—Gold yellow.

*Styles.*—Short, bunched, even.

*Stigmas.*—Brown.

*Ovaries.*—Enclosed.

Fruit: Appears to be infertile.

*Plant*

Form: Shrub, grandiflora type.

Growth: Very vigorous, upright, tall, many canes, compact.

Foliage: 3, 5 leaflets.

*Size.*—Large to medium.

*Quantity.*—Normal.

*Color.*—New foliage, light green. Under side, light green. Old foliage, normal green and under side is lighter.

*Shape.*—Oval.

*Texture.*—Glossy, smooth. Underside—smooth.

*Ribs and veins.*—Ordinary, to slightly prominent.

*Edge.*—Smooth serrated.

*Serration.*—Small.

*Leaf stem.*—Color light green. Underside prickles.

*Stipules.*—Medium to long, serrated.

*Disease resistance.* — Good resistance to mildew, black spot and rust.

Wood:

*New wood.*—Light green. Bark—smooth.

*Old wood.*—Color light green. Bark—smooth.

Thorns:

*Quantity.*—Very few.

*Form.*—Narrow base, hooked downward, medium length.

*Color.*—When young, green and red.

*Position.*—Irregular and in pairs.

*Prickles.*—Few.

*Color.*—Red.

*Short needles.*—Few (smooth stem).

Having thus disclosed my discovery, I claim:

A new and distinct variety of rose plant of the hybrid tea class as herein shown and described characterized particularly as to novelty by its vigorous habit of growth, good resistance to disease and dampness, abundant flowers, its large full blooms of excellent form, and the distinctive two-toned color of its flowers, the cream-white petals of which as the bud opens assume at the free edges thereof a delicate pink color which deepens as the petals age and enlarges toward but short of the bases of the petals.

No references cited.

ABRAHAM G. STONE, *Primary Examiner.*

R. E. BAGWILL, *Assistant Examiner.*